(12) United States Patent
Otto

(10) Patent No.: US 6,907,105 B2
(45) Date of Patent: Jun. 14, 2005

(54) METHODS AND APPARATUS FOR PLANNING AND DELIVERING INTENSITY MODULATED RADIATION FIELDS WITH A ROTATING MULTILEAF COLLIMATOR

(75) Inventor: Karl Otto, Vancouver (CA)

(73) Assignee: BC Cancer Agency, Vancouver (CA)

(*) Notice: Subject to any disclaimer, the term of this patent is extended or adjusted under 35 U.S.C. 154(b) by 33 days.

(21) Appl. No.: 10/253,781

(22) Filed: Sep. 25, 2002

(65) Prior Publication Data

US 2003/0086530 A1 May 8, 2003

Related U.S. Application Data

(60) Provisional application No. 60/324,266, filed on Sep. 25, 2001.

(51) Int. Cl.$^7$ .............................. A61N 5/10; G21K 1/04
(52) U.S. Cl. .......................... 378/65; 378/64; 378/151; 378/152
(58) Field of Search .......................... 378/64, 65, 147, 378/150, 151, 152

(56) References Cited

U.S. PATENT DOCUMENTS

| | | | | |
|---|---|---|---|---|
| 4,868,843 | A | | 9/1989 | Nunan .......................... 378/152 |
| 4,868,844 | A | | 9/1989 | Nunan .......................... 378/152 |
| 5,332,908 | A | | 7/1994 | Weidlich ................. 250/492.1 |
| 5,591,983 | A | | 1/1997 | Yao .......................... 250/505.1 |
| 5,663,999 | A | * | 9/1997 | Siochi .......................... 378/65 |
| 5,748,703 | A | | 5/1998 | Cosman ....................... 378/152 |
| 5,757,881 | A | | 5/1998 | Hughes ......................... 378/65 |
| 5,802,136 | A | | 9/1998 | Carol .......................... 378/65 |
| 5,818,902 | A | | 10/1998 | Yu ............................. 378/65 |
| 6,038,283 | A | | 3/2000 | Carol et al. .................... 378/65 |
| 6,052,430 | A | | 4/2000 | Siochi et al. .................. 378/65 |
| 6,108,400 | A | | 8/2000 | Siochi .......................... 378/65 |
| 6,134,296 | A | * | 10/2000 | Siochi .......................... 378/65 |
| 6,142,925 | A | | 11/2000 | Siochi et al. .................... 600/1 |
| 6,240,161 | B1 | | 5/2001 | Siochi .......................... 378/65 |
| 6,260,005 | B1 | | 7/2001 | Yang et al. .................... 703/11 |
| 6,278,766 | B1 | | 8/2001 | Kooy et al. .................. 378/147 |
| 6,314,159 | B1 | * | 11/2001 | Siochi .......................... 378/65 |
| 6,330,300 | B1 | | 12/2001 | Siochi .......................... 378/65 |
| 6,335,961 | B1 | | 1/2002 | Wofford et al. ............... 378/65 |
| 6,349,129 | B1 | * | 2/2002 | Siochi .......................... 378/65 |
| 6,393,096 | B1 | | 5/2002 | Carol et al. .................... 378/65 |
| 6,473,490 | B1 | * | 10/2002 | Siochi .......................... 378/65 |
| 6,504,899 | B2 | * | 1/2003 | Pugachev et al. ............. 378/65 |
| 6,560,311 | B1 | * | 5/2003 | Shepard et al. ............... 378/65 |
| 6,757,355 | B1 | * | 6/2004 | Siochi .......................... 378/65 |
| 2002/0006182 | A1 | | 1/2002 | Kim et al. ..................... 378/65 |

FOREIGN PATENT DOCUMENTS

| | | |
|---|---|---|
| WO | WO 99/48558 | 9/1999 |
| WO | WO 00/15299 | 3/2000 |
| WO | WO 01/60236 | 8/2001 |
| WO | WO 02/24277 | 3/2002 |

* cited by examiner

*Primary Examiner*—Allen C. Ho
(74) *Attorney, Agent, or Firm*—Oyen Wiggs Green & Mutala

(57) ABSTRACT

A method and system for controlling the spatial distribution of radiation produced by a radiation device having a multi-leaf collimator can generate arbitrary intensity-modulated radiation fields. The methods control both angles and leaf configuration of the multi-leaf collimator for each of multiple sub-fields. The leaf positions, collimator angles, and individual sub-field contributions may be derived by optimization techniques.

67 Claims, 6 Drawing Sheets

US 6,907,105 B2

METHODS AND APPARATUS FOR PLANNING AND DELIVERING INTENSITY MODULATED RADIATION FIELDS WITH A ROTATING MULTILEAF COLLIMATOR

CROSS-REFERENCE TO RELATED APPLICATION

The benefit of the filing date of U.S. provisional patent application Ser. No. 60/324,266 filed on Sep. 25, 2001 and entitled INTENSITY MODULATION USING A ROTATING MULTILEAF COLLIMATOR is claimed herein. The text and drawings of U.S. provisional patent application No. 60/324,266 are hereby incorporated by reference herein.

TECHNICAL FIELD

The invention relates to the field of radiotherapy and in particular to the delivery of radiotherapy by way of a radiotherapy device equipped with a multi-leaf collimator. The invention relates to radiotherapy devices and to systems and methods for controlling radiotherapy devices to deliver radiation treatments.

BACKGROUND

In radiation therapy a radiotherapy device is used to generate a source of radiation for the treatment of patients. The device may comprise a linear accelerator, for example. A typical radiotherapy device is mounted on a rotating gantry that allows radiation beams focused on a target to intersect the patient at varying orientations. Radiation to healthy tissue and organs must be restricted to avoid detrimental effects to the patient. The amount of radiation that can be concentrated on the target is limited by the need to limit the radiation dosage received by normal tissue surrounding the target.

A beam-shielding device modifies the spatial distribution of the radiation beam by selectively blocking areas where lower amounts of radiation are desired. A multileaf collimator is commonly provided in the path of the radiation beam for this purpose. The multileaf collimator shapes the radiation beam. The multileaf collimator has two opposing banks of adjacent blocking leaves. The leaves can each be moved in and out of the radiation beam to define arbitrary field shapes. The multileaf collimator can be used to shape the radiation beam so that it roughly matches the shape of the target area.

A method known as intensity modulation may be used to tailor a radiation field to further reduce the amount of radiation received by healthy tissue. This method provides a radiation field which has a non-uniform intensity over its spatial extent. A complete treatment may comprise the delivery of an different intensity modulated radiation field from each of a plurality of gantry angles.

A non-uniform field may be delivered by delivering radiation in each of a set of uniform sub-fields, each having a different multileaf collimator configuration. Intensity modulated fields may be delivered using static or dynamic methods. In static methods each sub-field is shaped while the radiation beam is off and then a radiation sub-field is delivered once the leaves are in position. In dynamic methods the leaves are moved while the beam is on.

The multileaf collimator has certain characteristics that limit its ability to protect healthy tissue from exposure to radiation. Because each leaf has a finite width, the precision at which the radiation beam can be spatially controlled is limited to that width in that dimension. The multileaf collimator is constructed such that each leaf is as close as possible to its adjacent leaf to avoid the leakage of radiation in between them. Still, the leaves are not perfectly in contact at all times and there is some radiation that will leak through the gap between them. To avoid this problem, adjacent leaves can be constructed with a tongue and groove shape on each side. Although the amount of leakage radiation is reduced some radiation still leaks through, damaging healthy tissue. Also, the tongue and groove creates unwanted under-dosing effects to the target for some intensity modulated fields.

When delivering intensity modulated fields it is in general necessary to have the radiation device produce more radiation and for a longer period of time than for an un-modulated field. The amount of time it takes to treat a patient is increased, reducing the number of patients that can be treated per day. This also has implications on treatment room radiation shielding requirements, necessitating additional shielding for new and existing rooms.

Multileaf collimators are constructed with enough leaves to cover a given length (e.g. 40 cm). Due to mechanical limitations, the range of leaf motion is restricted to a fraction of that length. The maximum intensity modulated field size is therefore limited to a rectangle whose width is given by the range of leaf motion.

There is a need for methods and apparatus for delivering radiation which minimize the dosage delivered to healthy tissue. There is a particular need for such methods and apparatus which can be practiced in existing radiotherapy devices without requiring extensive expensive modifications.

SUMMARY OF THE INVENTION

The invention relates to methods and apparatus for controlling radiotherapy devices. One aspect of the invention provides a method for determining a set of configurations for a multileaf collimator in a radiotherapy device for production of a desired radiation field. The method comprises varying a parameter of an initial set comprising three or more multileaf collimator configurations to provide a varied set of multileaf collimator configurations. Typically each configuration in the initial set comprises a different angle of rotation for the collimator. The method then determines a calculated radiation field resulting from the varied set of multileaf collimator configurations. Based upon the calculated radiation field, the method determines whether one or more acceptance criteria are satisfied. If the acceptance criteria are satisfied, the method makes a further variation to the varied set of multileaf collimator configurations. This is repeated until the varied set of multileaf collimator configurations satisfies one or more termination criteria.

Other aspects of the invention provide apparatus for determining a set of configurations for a multileaf collimator in a radiotherapy device. The apparatus comprises a data processor and computer software which, when executed by the data processor causes the data processor to execute a method of the invention.

The invention may also be embodied in a computer readable medium which comprises computer-readable instructions which, when executed by a data processor, cause the data processor to execute a method of the invention.

A further aspect of the invention provides a method for controlling a radiation device to deliver a radiation field having a desired spatial distribution of radiation. The method comprises delivering in succession at least three radiation sub-fields, each of the sub-fields shaped by a multileaf collimator and rotating the collimator to a different angular position for the delivery of each of the sub-fields.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention provides a method for controlling a radiotherapy device to deliver a desired radiation field in a treatment area within a patient. The method involves creating the desired radiation field by sequentially exposing the patient to a number of sub-fields. Each sub field has a shape defined by a multileaf collimator. The multi-leaf collimator is rotated between the different sub fields.

Figure 1:
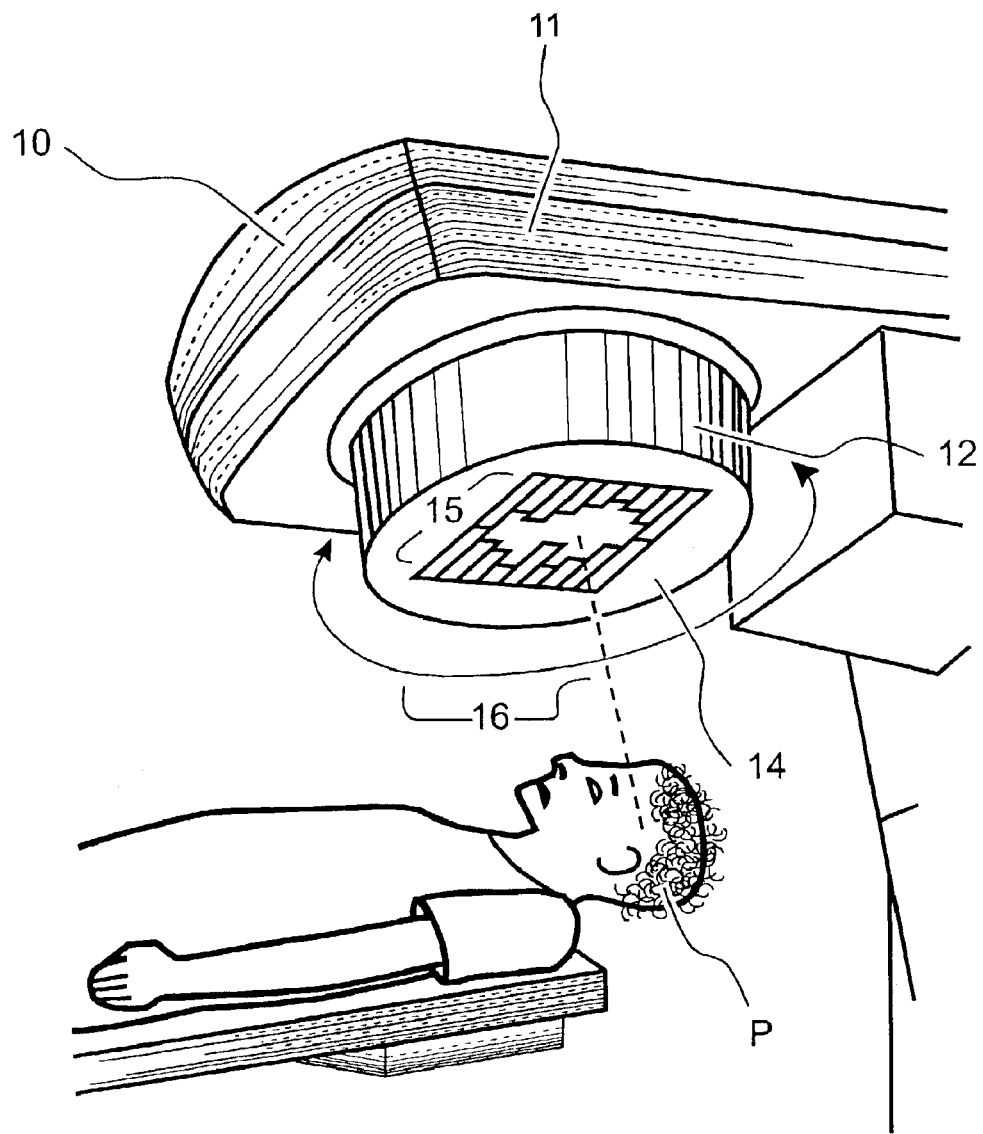
FIG. 1 is a simplified schematic diagram of the radiation emitting portion of a radiation treatment device with a rotating multileaf collimator.

FIG. 1 illustrates a patient P positioned to receive radiation from a radiotherapy device 10. Radiation is emitted from a source (not shown) in a portion 11 of the radiotherapy device. Radiation from the source exits through a collimator 12 and impinges onto patient P. A multi-leaf collimator 14 is housed in collimator 12. Multi-leaf collimator 14 has multiple movable leaves 15. Leaves 15 are shown in an exemplary configuration in FIG. 1. Radiotherapy device 10 includes a mechanism (not shown) for rotating multi-leaf collimator 14 about an axis in the plane of leaves 15 as indicated by arrow 16.

Radiotherapy device 10 comprises a control system which is coupled to control mechanisms which move leaves 15 and rotate multi-leaf collimator 14. The control system can place multileaf collimator 14 in any allowable configuration. The control system typically comprises a computer processor which receives parameters specifying the leaf positions and rotation angle for a sub field and actuates the mechanisms to cause the leaves to move to the desired positions and to cause the multi-leaf collimator to be rotated to the desired angle.

For each sub-field, the controller operates the radiation source to produce radiation. The radiation passes through collimator 12 and is shaped by multileaf collimator 14. The shaped radiation impinges onto the patient P. The total radiation dosage delivered at a point in the patient from several sub fields is the sum of the radiation dosage delivered by each sub field individually. Therefore a radiation field which closely approximates an ideal radiation field can be delivered by delivering several appropriately configured sub-fields at different times.

Figure 2A:
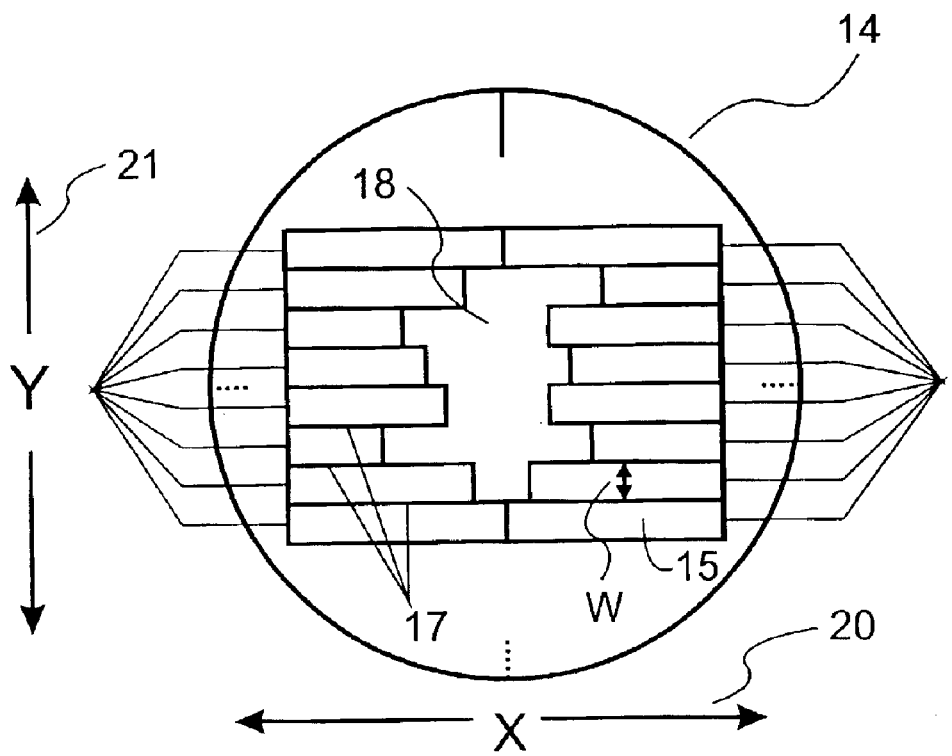
FIGS. 2A and 2B are simplified top view illustrations of a multileaf collimator at two separate angulations and leaf configurations.
Figure 2B:
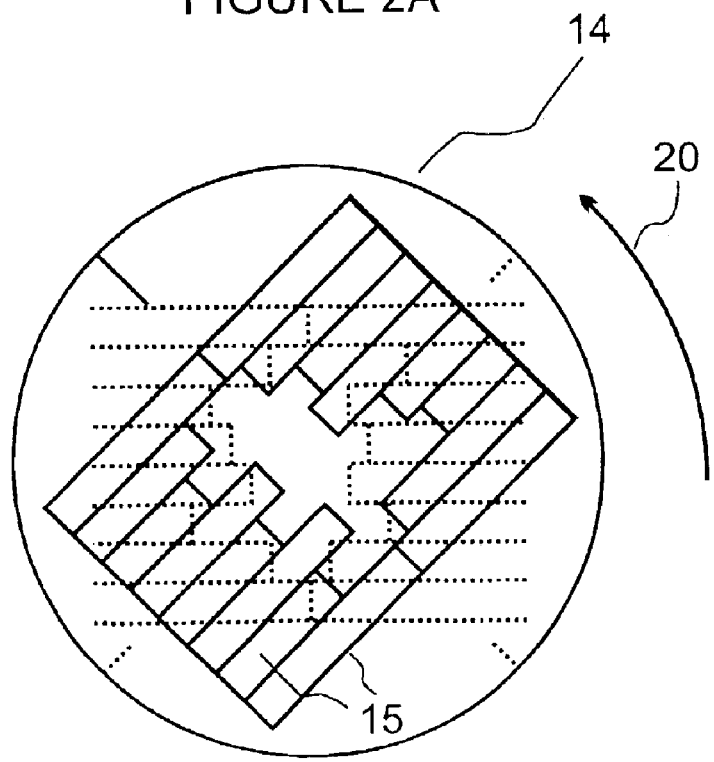

FIGS. 2A and 2B illustrate a simplified schematic view of multileaf collimator 14 at two configurations. Each of the two configurations has a different rotation angle. Leaves 15 are shown in an exemplary configuration and are not limited to the number or shape shown in FIGS. 2A and 2B. A typical multileaf collimator has many more leaves than illustrated. Leaves 15 may all have equal widths, W, as illustrated or may vary in width. Some multi-leaf collimators have narrower leaves in their central portions and wider leaves in their outer portions.

Leaves 15 may be adjusted to block radiation which would not pass through an area to which it is desired to deliver radiation. Leaves 15 are movable longitudinally so that the shape of the treatment area 18 can be modified. The leaf configurations of FIGS. 2A and 2B each define a sub-field. These sub-fields can be added to each other and to other sub-fields to build up an arbitrary spatial distribution of radiation. In a typical intensity modulated radiation treatment a number of sub-fields are configured to produce an overall spatial distribution of radiation which matches a desired radiation distribution very closely.

Each of leaves 15 can be moved longitudinally (i.e. in the x-direction 20) but not transversely (i.e. not in y-direction 21). Because individual leaves 15 are only able to move longitudinally, the maximum spatial resolution with which the shape of any sub-field can be specified in y-direction 21 is limited by the width of each individual leaf 15. Leaves 15 typically have widths such that each leaf blocks a strip of radiation about 0.5 cm wide to about 1 cm wide at the treatment area. Typically some radiation is transmitted between adjacent leaves 15 outside of the desired field shape. This "leakage" results in some radiation being delivered along edges 17 of leaves 15 where, ideally, all radiation would be blocked. Where adjacent leaves interlock with one another to minimize radiation leakage, for example, by providing a tongue on one leaf and a complementary groove on a neighboring leaf, the amount of radiation delivered at leaf edges which protrude into the field shape 18 can be smaller than would normally be desired.

FIG. 2B illustrates multileaf collimator 14 in a different configuration from that shown in FIG. 2A. Both the leaf configuration and rotational angle differ between the configurations of FIGS. 2A and 2B. In FIG. 2B, collimator 14 has been rotated through an angle $\ominus$ relative to the configuration of FIG. 2A. The dotted lines in FIG. 2B are an overlay which show the leaf positions of the configuration of FIG. 2A. The configurations of FIGS. 2A and 2B are examples of sub-fields that are rotated relative to one another and could be used to generate an intensity modulated field. More sub-fields would be used to generate a typical intensity modulated field. For typical intensity modulated fields at least 5, and more typically 8 or more sub-fields are used.

Because multileaf collimator 14 is rotated between sub-fields, the limited spatial resolution resulting from the finite width of leaves 15 is in a different direction for each sub-field. By combining several appropriately configured sub-fields, each with a different rotation angle, the method of the invention can generate spatial distributions of radiation with a spatial resolution that is smaller than the leaf width in all directions.

Since rotating multileaf collimator 14 moves the positions of the edges of leaves 15, any radiation leakage between the leaf edges occurs in different positions for each sub-field. This leakage radiation is therefore distributed over an area instead of being repeatedly delivered at the same set of locations. This causes less damage to healthy tissue.

Furthermore, because the leaf edges move with each sub-field it is possible to compensate for leakage radiation by blocking areas which receive leakage radiation in other sub-fields. Areas which may receive less radiation than desired in one sub field because they are along leaf edges can be exposed to more radiation in other sub fields to compensate.

Radiation sub-fields may be delivered statically (with the collimator not rotating while radiation is being delivered) or dynamically (with the collimator rotating while radiation is being delivered).

Figure 3:
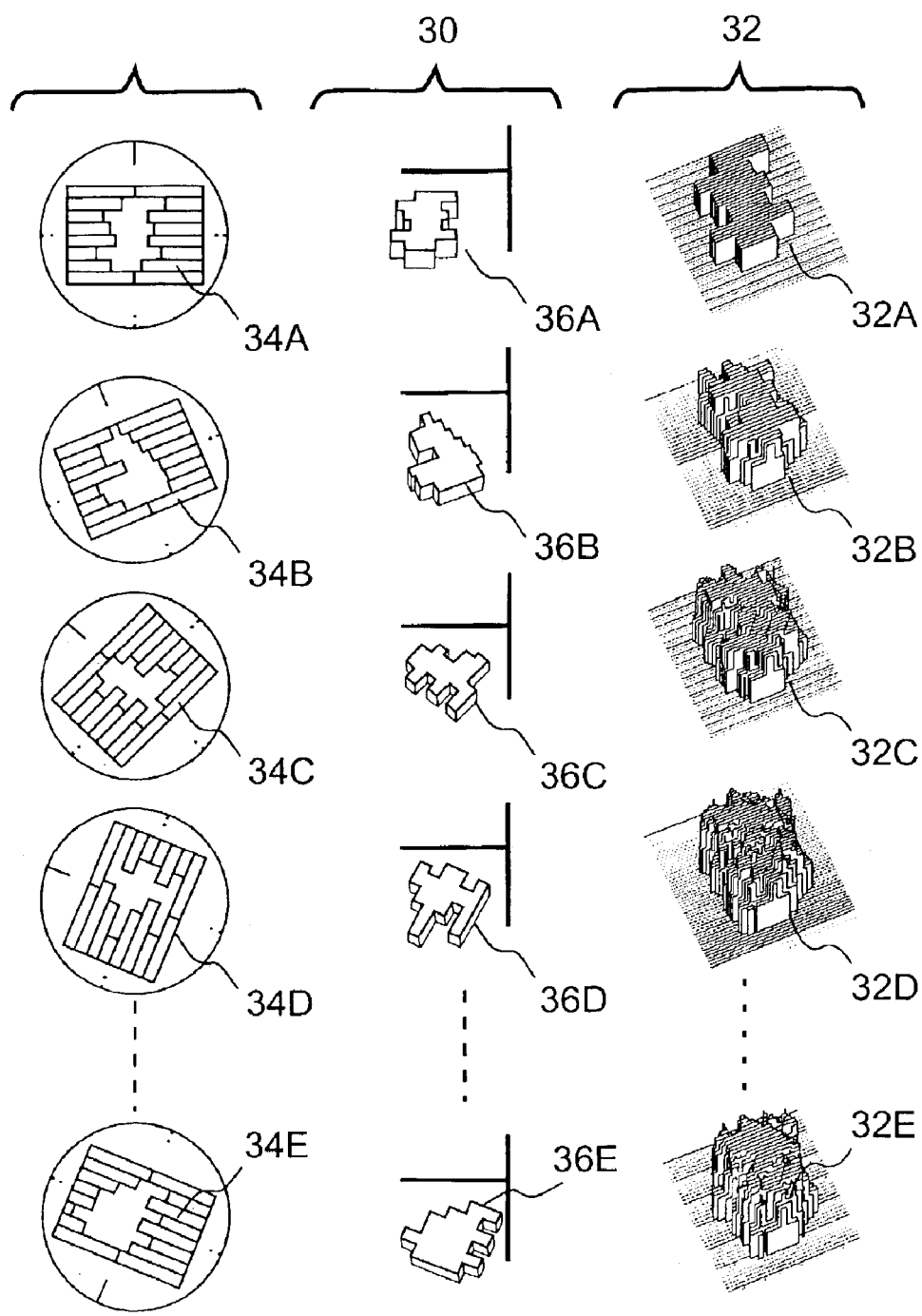
FIG. 3 illustrates a method for generating intensity modulated radiation fields with arbitrary spatial distributions according to the invention.

FIG. 3 illustrates several example configurations for a multileaf collimator, the distribution of radiation 30 in the sub-field delivered when each configuration is used and the cumulative spatial distribution of radiation 32 that results when that sub-field is added to the radiation dose delivered by previous sub-fields.

The first collimator shape 34A provides a first sub-field, which is a 2-dimensional surface 36A of uniform radiation intensity having a shape which matches shape 34A. Delivery of sub-field 36A results in a spatial radiation distribution 32A. The second multileaf collimator shape 34B is rotated relative to shape 34A and has a different leaf configuration. Second shape 34B also generates a uniform-intensity sub-field 36B. The cumulative spatial distribution of radiation 32B for the first two sub-fields provides a simple spatial distribution of radiation of limited complexity. Further sub-fields 36B, 36D and 36E are added. The addition of sub-fields 36C and 36D yields cumulative spatial distributions 32C and 32D. After adding sub-field 36E, until the desired intensity-modulated field 32 is achieved.

The invention permits building radiation fields in which the overall field width is not limited by the range of leaf movement.

It is relatively straightforward to add together radiation doses delivered by each of a number of given sub-fields to yield an overall radiation field. In practice, however, the desired overall radiation field is the starting point. The desired overall radiation field is derived by a treatment planning system in response to a prescription specified by a physician. It is not trivial to identify a combination of sub-fields which will produce a desired overall radiation field when collimator 14 is permitted to rotate between sub-fields.

Figure 4:
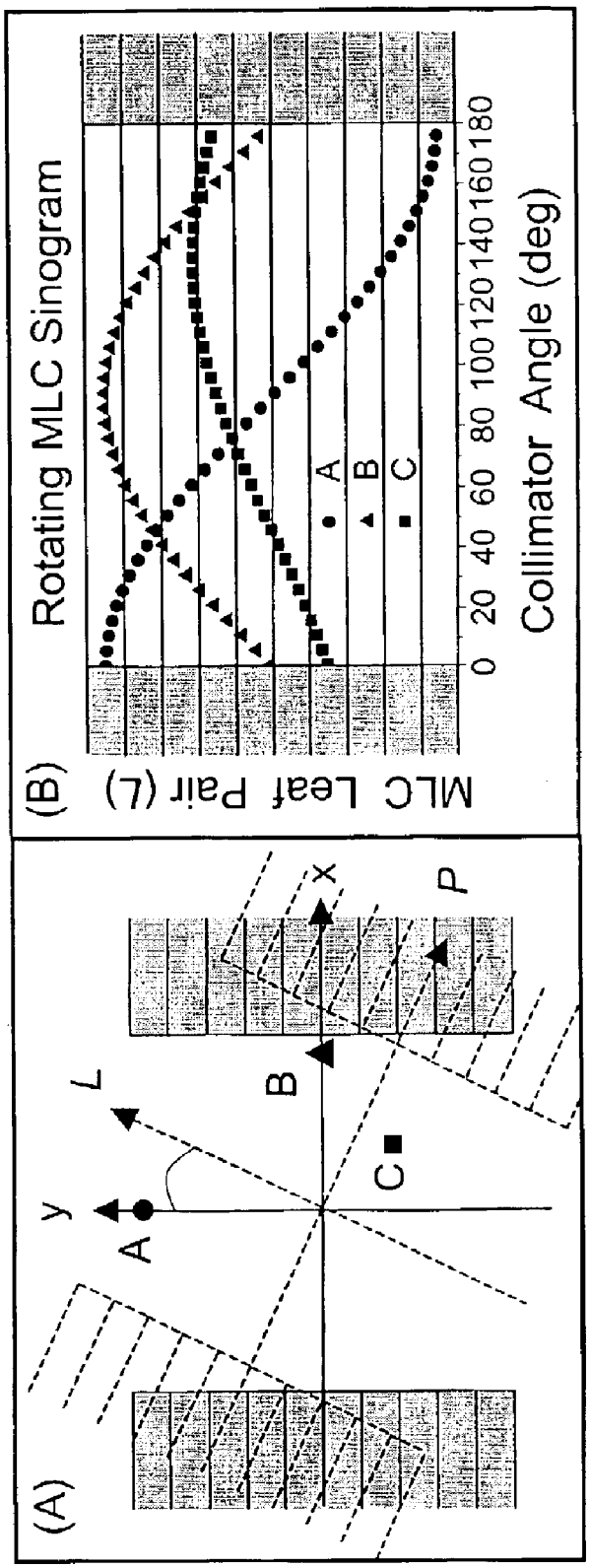
FIG. 4 is a plot illustrating the trajectory of points on a multileaf collimator which correspond to points in a treatment field as the multileaf collimator is rotated.

Each leaf will affect different locations in the overall radiation field depending upon its location, position and the angle of collimator 14. For a desired point (x, y) in the overall radiation field, the leaf pair, L, and leaf position, P, that intersect that point are given by:

$$L = x \sin \theta + y \cos \theta \quad (1)$$

$$P = x \cos \theta - y \sin \theta \quad (2)$$

where θ is the rotation angle of multi-leaf collimator 14. As collimator 14 is rotated the leaf pairs capable of modulating the radiation delivered at a specific point change. FIG. 4 is a sinogram showing the trajectories of three points in the treatment field relative to the leaves in collimator 14 as collimator 14 is rotated.

As collimator 14 is rotated, each point follows a sinusoidal trajectory through the leaf pairs. The amplitude of each trajectory depends upon a radial distance of the point from a center of rotation of collimator 14. The phase of each trajectory depends upon the initial position of the point along collimator 14. In FIG. 4, points A and B are located equal distances from the center of rotation of collimator 14 and trace trajectories with equal amplitudes but different phases.

Any desired overall radiation field can be made by applying any of many possible combinations of sub-fields. One can select from these a combination of sub fields that will produce the desired overall intensity modulated field with the smallest total output of the radiation source.

Figure 5:
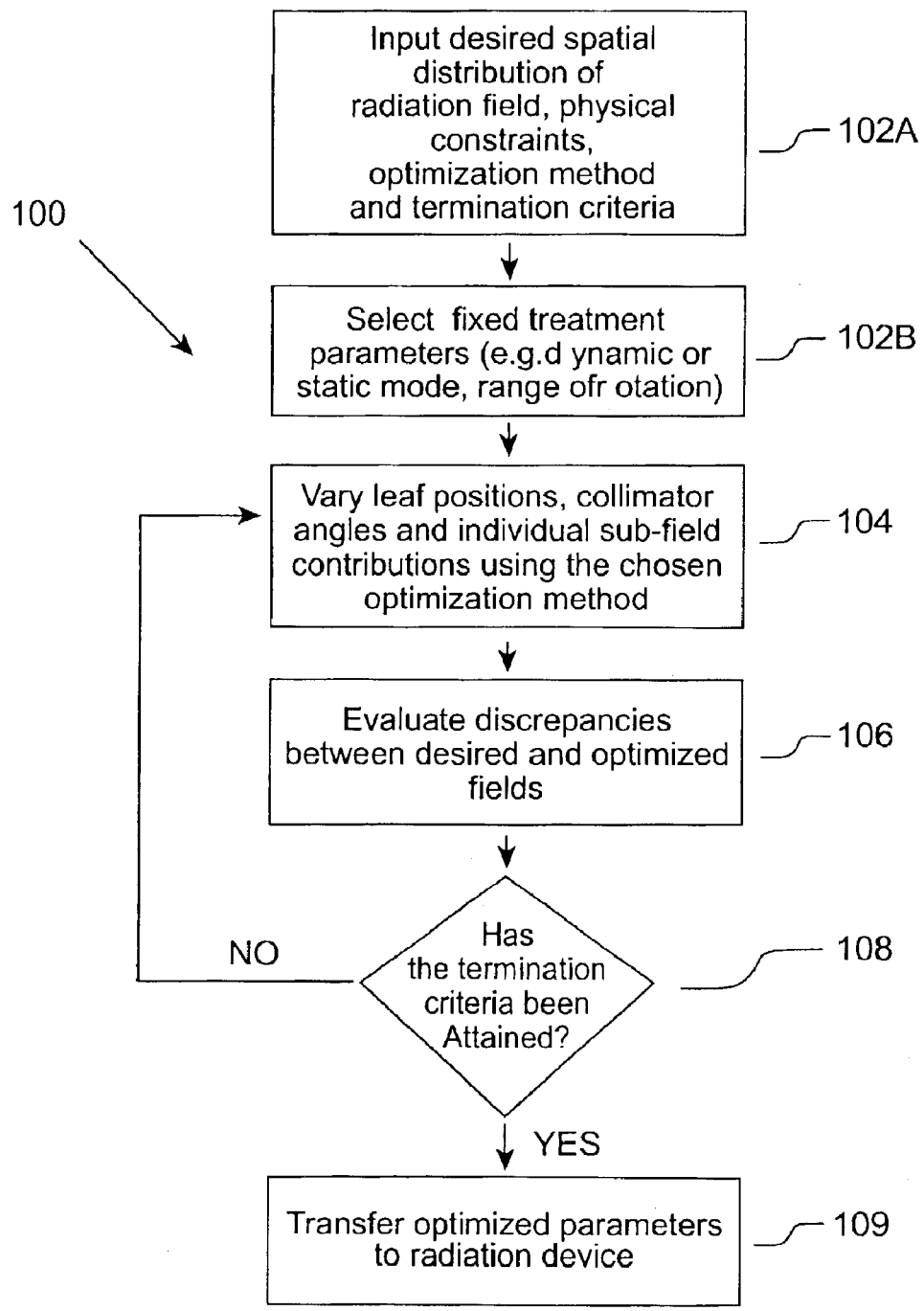
FIG. 5 is a flowchart illustrating a method for deriving rotated multileaf collimator configurations according to one embodiment of the invention; and, FIG. 6 is a flowchart illustrating an optimization process for a particular embodiment of the invention.

FIG. 5 is a flowchart which illustrates a method 100 which may be used to identify a set of sub-fields which will produce a desired overall radiation field. Method 100 may be performed on a treatment planning computer system or on another suitable programmed data processing device. Method 100 is initialized in blocks 102A and 102B. In block 102A the desired overall radiation field is provided. The desired overall radiation field may be specified in output from treatment planning software.

Block 102A also provides any mechanical and physical constraints which must be observed. For example, in a particular multileaf collimator:

the leaves may be movable over only limited ranges, adjacent leaves may be constrained to have positions within certain distances from one another, opposing leaves may be forbidden to overlap with one another, it may be necessary to maintain a minimum gap between opposing leaves, and, in dynamic delivery the leaves may have a maximum velocity, or the like.

Block 102A may also permit selection among a set of available optimization routines and termination criteria. Many different optimization methods or termination criteria may be used.

Block 102B may permit an operator to optionally specify values for certain parameters. Any parameters that affect the leaf positions and the multileaf collimator rotation may be selected as fixed. Some typical examples include, but are not limited to, whether the radiation is to be delivered statically or dynamically, the maximum range of rotation of the collimator and the maximum number of sub-fields. As another example, the angle of rotation of the multileaf collimator could be specified for one or more, or all, sub-fields.

Block 104 determines a set of configurations for delivering a number of sub-fields. Each configuration specifies leaf positions, collimator angles and sub-field contributions. All the parameters that are not fixed may be varied according to the chosen optimization method.

Block 106 evaluates any discrepancies between the calculated spatial distribution of radiation resulting from the configurations determined in block 104 and the desired spatial distribution of radiation. Block 106 may do this by summing the radiation contribution delivered to each point in the radiation field over all of the sub-fields. Instead of summing over all sub fields block 106 may calculate the spatial distribution of radiation by identifying pixels in the calculated field which are affected by a most recent change in leaf positions and adding or subtracting an appropriate amount to the total amount of radiation which the overall radiation field will deliver to those pixels.

It is convenient to compute in advance the correspondence between leaf position and points in the radiation field for all possible angles of collimator 14. This information may be provided in a lookup table. This can speed the calculations since the pixels affected by a change in leaf position can be identified with a lookup instead of a more complicated calculation.

The discrepancies between the calculated and desired radiation fields can be measured using any suitable metric. For example, the sum of absolute differences (SAD) between the calculated and desired radiation fields may be used as a measure of the discrepancies. If the discrepancies are acceptable and the termination criteria has been attained then configuration information including leaf positions, collimator angles and individual sub-field contributions is stored or transferred to radiation device 10 for patient treatment. If the termination criteria has not been attained as determined in block 108, then method 100 returns to block 104 for further optimization. Method 100 continues in this fashion until the termination criteria have been attained or the discrepancies between the desired and optimized treatments no longer improve. If the termination criteria are obtained then the treatment parameters may be transferred to a radiation device in block 109.

Figure 6:
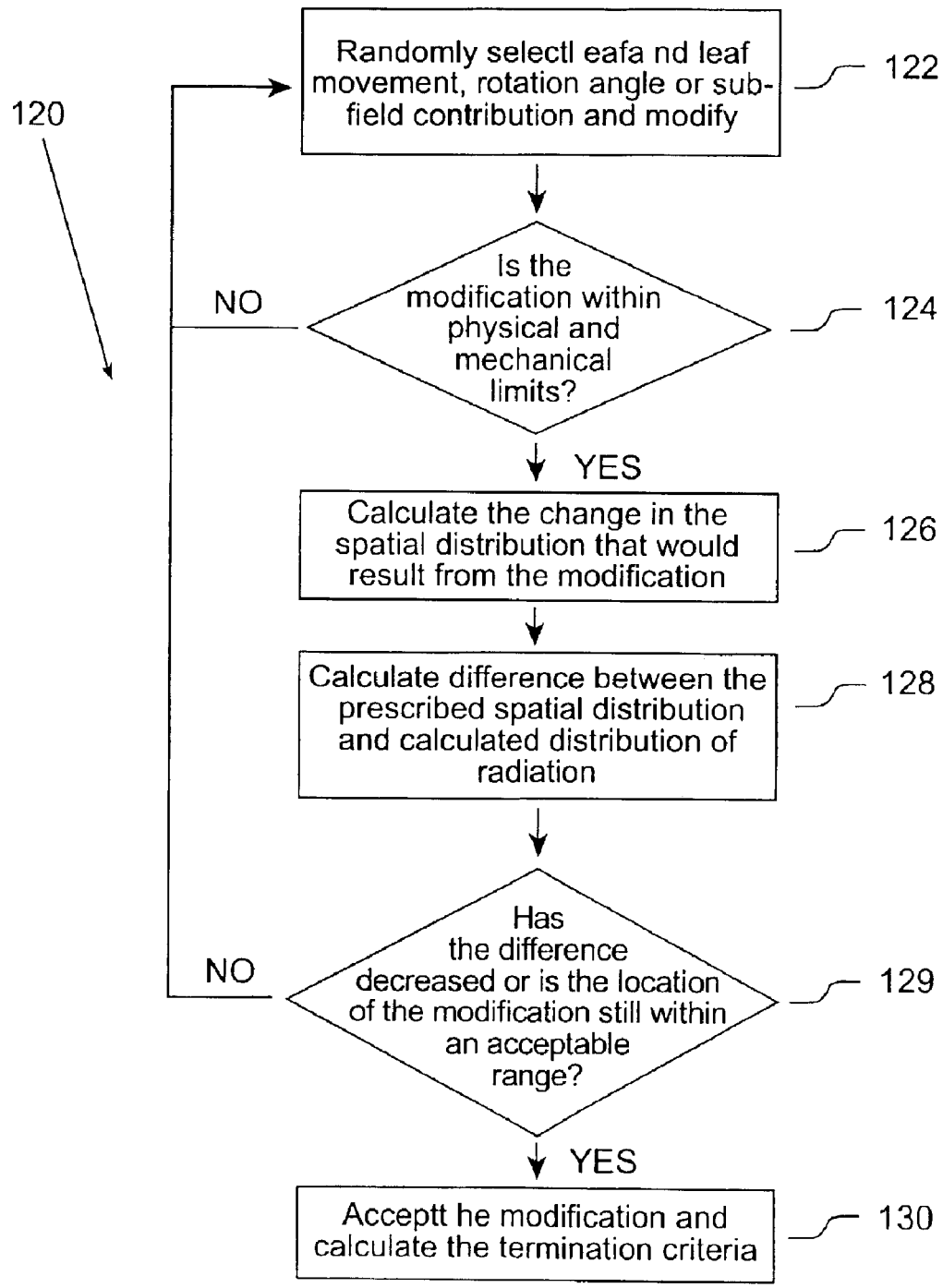

FIG. 6 is a flowchart illustrating an optimization process 120 that may be used in the invention. Process 120 is an example of one way to implement block 104. Process 120 begins with an initial set of configurations. The initial set of configurations may, for example, comprise a specified leaf configuration for each of a number of sub fields, each of the sub-fields having a rotational angle with the rotational angles of the sub-fields distributed over an angular range spanning at least 90 degrees. Preferably the angular range spans more than 90 degrees. Most preferably the angular range spans 160 or more degrees. Increasing the rotation range past 270 degrees could be done but typically yields little benefit.

The initial set of configurations may be at equally spaced apart angles. For example, the initial set of configurations may comprise 10 configurations oriented at angles of 0, 20, 40, . . . , 180 degrees. Each initial configuration specifies position of leaves 15. In an embodiment of the invention preferred for static delivery, each opposing pair of leaves is initialized to be closed and to meet over an area in the desired overall radiation distribution where the desired dosage is larger than at other areas in the trajectory of the pair of leaves. This has the advantage that whenever a leaf is moved from its initial position the resulting opening exposes a region that requires the most radiation. This embodiment is not suitable for dynamic delivery in cases where the same pair of leaves would be initialized to very different locations for subsequent sub-fields. Depending upon the maximum leaf velocity it may not be possible to move the leaves quickly enough to move between the positions in the time between sub-fields.

Another initialization configuration places all of the leaves in a closed configuration with opposing pairs of leaves meeting at a centerline of multileaf collimator 14.

In block 122, process 120 selects a parameter to be varied. The parameter is preferably randomly selected from a set of available parameters. The set of available parameters may include:

the position of each leaf for each sub-field;

the collimator angle for each sub field;

the radiation contribution for each sub-field.

The selected parameter is varied by an amount. The amount may be chosen randomly. The amount may be chosen randomly within a permitted range.

Block 124 determines whether the modification is physically possible (i.e. that it does not exceed the mechanical limitations of the multileaf collimator 14). If block 124 determines that the modification is not allowed then method 120 returns to block 122 and attempts another modification. Blocks 122 and 124 may be combined in that block 122 may operate to vary the chosen parameter only within a range of values which are physically realizable.

If block 124 determines that the modification is possible then method 120 proceeds to block 126 which determines the spatial distribution of radiation that would result if the modification were made. Block 128 computes a discrepancy between the desired spatial distribution of radiation and the spatial distribution of radiation computed in block 126. The discrepancy may be measured by computing a SAD or other difference metric between the desired spatial distribution of radiation and the spatial distribution of radiation computed in block 126. Block 128 then determines whether a set of one or more acceptance criteria is satisfied. In a currently preferred embodiment of the invention, the acceptance criteria are satisfied if either:

the difference has decreased relative to the previous iteration; or, in the case of a change in leaf position, the differences at the pixels affected by that change are within an acceptable range.

If the acceptance criteria are satisfied at block 129 then, the modification is accepted and the method proceeds to block 130. Otherwise, the modification is not accepted and method 120 returns to block 122.

The acceptable range used by the acceptance criteria may have a larger value at the start of method 120 and may be reduced one or more times as method 120 progresses.

In block 130 method 120 checks to see whether a termination criteria is satisfied. If so, method 120 terminates. If not, method 120 returns to block 122 for further optimization. The termination criteria may, for example:

require that the calculated radiation field must not exceed the desired radiation field at any point by more than a first threshold amount (the first threshold may be 3% of the desired radiation field, for example);

require that the calculated radiation field must not be less than the desired radiation field at any point by more than a second threshold amount (the second threshold may be the same as the first threshold); and, require that the amount of radiation delivered to tissues outside the treatment area be kept below a third threshold amount.

Dynamic treatment may be achieved by providing a large number of sub-fields separated from one another by small angular increments. The angular increments may be, for example, in the range of less than 0.2 degrees to 2 degrees and preferably do not exceed about 3 to 4 degrees. In developing a set of configurations for dynamic delivery of radiation it can be desirable to commence with a few sub-fields and to increase the number of sub-fields as the method proceeds.

For example, the method may begin by initializing 10 sub-fields with collimator angles that are spaced apart equally over a suitable angular range. After a number of iterations it may be found that additional iterations do not yield significant improvement. At this point, additional sub-fields may be added. For example, if more than a given number of iterations has occurred with the SAD improving by less than a threshold amount then the number of sub-fields may be increased. In one embodiment of the invention the number of sub-fields is increased when 10,000 iterations have passed with the SAD decrease not exceeding 0.1%. Of course, a different number of iterations could be used to trigger a change in the threshold amount.

One way to increase the number of sub-fields is to add an additional sub-field which has a collimator angle intermediate (preferably half way) between each existing pair of sub-fields. The additional sub-fields can have initial leaf positions which are linearly interpolated between the leaf positions of the angularly adjacent sub-fields. The optimization then continues as described above. After the number of sub-fields has been doubled a number of times all sub-fields required to provide a dynamic treatment will be specified.

The acceptable range provided in the acceptance criteria may be changed at the same time additional sub-fields are introduced. For example, in a current embodiment of the invention the acceptable range is halved each time the angle between adjacent sub-fields is halved. After all of the sub-fields have been added the acceptable range may be further reduced until no more improvement is noted.

Certain implementations of the invention comprise computers or other data processors which execute software instructions which cause the processors to perform a method of the invention. For example, the invention may be embodied in a computer-based treatment planning system which performs methods according to the invention for defining angles and leaf positions for a plurality of sub-fields to be used to deliver a desired radiation field to a patient. The invention may also be provided in the form of a program product. The program product may comprise any medium which carries a set of computer-readable signals comprising instructions which, when executed by a computer processor, cause the data processor to execute a method of the invention. The program product may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like or transmission-type media such as digital or analog communication links.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

while the methods describe above randomly vary one parameter at a time, the methods may be modified to vary two or more parameters at a time.

while the foregoing description describes dynamic and static methods separately, the invention can be used to provide a treatment which combines dynamically varied radiation exposure through one or more ranges of angles with one or more statically provided sub fields. The statically provided sub-fields may have the multi-leaf collimator oriented at an angle which is within or outside of a range of angles covered by the dynamic phase.

while it may be convenient to provide multileaf collimator configurations which are at equally spaced apart angles, this is not generally necessary, particularly for static methods. Different angle spacings could also be used.

It will be appreciated by persons skilled in the art that the invention described in the above detailed description is not intended to be limited to what has been particularly shown or to the specific form set forth herein. It is intended that the scope of the present invention include both combinations and subcombinations of the features described herein as well as variations thereof which would occur to a person skilled in the art upon reading the description of the invention. Accordingly, the scope of the invention is to be construed in accordance with the substance defined by the following claims.

What is claimed is:

1. A method for determining a set of configurations for a multileaf collimator in a radiotherapy device for production of a desired radiation field, the method comprising:
   a) varying a parameter of an initial set comprising three or more multileaf collimator configurations to provide a varied set of multileaf collimator configurations;
   b) determining a calculated radiation field resulting from the varied set of multileaf collimator configurations;
   c) based upon the calculated radiation field determining whether one or more acceptance criteria are satisfied;
   d) if the acceptance criteria are satisfied making a further variation to the varied set of multileaf collimator configurations;
   e) if the acceptance criteria are not satisfied, rejecting a most recent variation to the varied set of multileaf collimator configurations; and,
   f) repeating (b) through (e) until the varied set of multileaf collimator configurations satisfies one or more termination criteria;
   wherein each of the multileaf collimator configurations comprises a different rotational angle for the multileaf collimator relative to a direction of a radiation beam to be delivered through the multi-leaf collimator.

2. The method of claim 1 wherein, in the initial set, the rotational angles for the multileaf collimator span a range of angles exceeding 90 degrees.

3. The method of claim 2 wherein, in the initial set, the rotational angles for the multileaf collimator are substantially equally spaced apart from one another.

4. The method of claim 1 wherein determining whether the acceptance criteria are satisfied comprises determining a difference between the calculated radiation field and the desired radiation field.

5. The method of claim 4 wherein determining a difference between the calculated radiation field and the desired radiation field comprises computing a sum of absolute differences between the calculated radiation field and the desired radiation field.

6. The method of claim 5 wherein determining whether one or more acceptance criteria are satisfied comprises determining whether the sum of absolute differences has decreased since a previous iteration.

7. The method of claim 5 wherein varying a parameter comprises moving a leaf position and determining whether one or more acceptance criteria are satisfied comprises determining whether, in an area affected by moving the leaf position, the calculated radiation field differs from the desired radiation field by an amount not exceeding a threshold amount.

8. The method of claim 1 comprising determining that the termination criteria are satisfied when no point in the calculated radiation field differs from a corresponding point in the desired radiation field by more than a threshold amount.

9. The method of claim 1 wherein determining the calculated radiation field comprises including in the calculated radiation field inter-leaf leakage radiation for each of the multileaf collimator configurations in the varied set.

10. The method of claim 1 wherein, when the termination criteria are satisfied, the varied set of collimator configurations includes a set of collimator configurations wherein the rotational angles of the collimator configurations are spaced apart by an angular separation not exceeding 3 degrees over a range of angles.

11. The method of claim 10 wherein the range of angles spans more than 90 degrees.

12. The method of claim 1 further comprising, after the termination criteria are satisfied, using the varied set of multileaf collimator configurations as input to a controller in a radiation device and, in any sequence, configuring a multileaf collimator of the radiation device according to each of the multileaf collimator configurations in the varied set of multileaf collimator configurations and, while the collimator of the radiation device is in each of the multileaf collimator configurations operating the radiation device to deliver radiation through the multileaf collimator.

13. The method of claim 12 wherein the varied set of collimator configurations includes a set of collimator configurations, the rotational angles of the collimator configurations are spaced apart by an angular separation not exceeding 3 degrees over a range of angles, and the method comprises operating the radiation device in a dynamic mode by continuing to deliver radiation through the multileaf collimator while sequentially configuring the collimator of the radiation device in each of the multileaf collimator configurations.

14. The method of claim 13 wherein the range of angles spans more than 90 degrees.

15. A method for determining a set of configurations for a multileaf collimator in a radiotherapy device for production of a desired radiation field, the method comprising:
   a) varying a parameter of an initial set comprising three or more multileaf collimator configurations to provide a varied set of multileaf collimator configurations.
   b) determining a calculated radiation field resulting from the varied set of multileaf collimator configurations;
   c) based upon the calculated radiation field determining whether one or more acceptance criteria are satisfied;
   d) if the acceptance criteria are satisfied making a further variation to the varied set of multileaf collimator configurations;
   e) if the acceptance criteria are not satisfied, rejecting a most recent variation to the varied set of multileaf collimator configurations; and,
   f) repeating (b) through (e) until the varied set of multileaf collimator configurations satisfies one or more termination criteria;
   wherein:
      each of the multileaf collimator configurations comprises a different rotational angle for the multileaf collimator relative to a direction of a radiation beam to be delivered through the multi-leaf collimator;
      determining whether the acceptance criteria are satisfied comprises determining a difference between the calculated radiation field and the desired radiation field;
      determining a difference between the calculated radiation field and the desired radiation field comprises computing a sum of absolute differences between the calculated radiation field and the desired radiation field; and,
      determining whether one or more acceptance criteria are satisfied comprises determining whether the sum of absolute differences has decreased since a previous iteration;
   the method comprising, before the one or more termination criteria are satisfied, adding one or more additional configurations to the varied set of multileaf collimator configurations.

16. The method of claim 15 wherein adding one or more additional configurations comprises adding an additional configuration having a rotational angle intermediate the rotational angles of a pair of adjacent configurations in the varied set of multileaf collimator configurations.

17. The method of claim 15 wherein adding one or more additional configurations comprises, for each pair of adjacent configurations in the varied set of multileaf collimator configurations, adding an additional configuration having a rotational angle intermediate the rotational angles of the pair of adjacent configurations.

18. The method of claim 17 wherein determining whether one or more acceptance criteria are satisfied comprises determining whether the sum of absolute differences has decreased since a previous iteration.

19. The method of claim 17 wherein varying a parameter comprises moving a leaf position and determining whether one or more acceptance criteria are satisfied comprises determining whether, in an area affected by the moving of the leaf position, the calculated radiation field differs from the desired radiation field by an amount not exceeding a threshold amount.

20. The method of claim 19 comprising, before the termination criteria are satisfied, reducing the threshold amount.

21. The method of claim 20 comprising reducing the threshold amount within 2500 iterations of adding an additional configuration.

22. A method for determining a set of configurations for a multileaf collimator in a radiotherapy device for production of a desired radiation field, the method comprising;
   a) varying a parameter of an initial set comprising three or more multileaf collimator configurations to provide a varied set of multileaf collimator configurations;
   b) determining a calculated radiation field resulting from the varied set of multileaf collimator configurations;
   c) based upon the calculated radiation field determining whether one or more acceptance criteria are satisfied;
   d) if the acceptance criteria are satisfied making a further variation to the varied set of multileaf collimator configurations;
   e) if the acceptance criteria are not satisfied, rejecting a most recent variation to the varied set of multileaf collimator configurations; and,
   f) repeating (b) through (e) until the varied set of multileaf collimator configurations satisfies one or more termination criteria;
      wherein each of the multileaf collimator configurations comprises a different rotational angle for the multileaf collimator relative to a direction of a radiation beam to be delivered through the multi-leaf collimator; and
      wherein in each of a plurality of the collimator configurations in the initial set, each of a plurality of opposing pairs of leaves is initialized to be closed and to meet at a point corresponding to an area in the desired overall radiation distribution where the desired dosage is larger than at other areas in a trajectory of the pair of leaves.

23. Apparatus for determining a set of configurations for a multileaf collimator in a radiotherapy device the apparatus comprising a data processor and computer software which, when executed by the data processor causes the data processor to execute a method comprising:
   a) varying a parameter of an initial set comprising three or more multileaf collimator configurations to provide a varied set of multileaf collimator configurations;
   b) determining a calculated radiation field resulting from the varied set of multileaf collimator configurations;
   c) based upon the calculated radiation field determining whether one or more acceptance criteria are satisfied;
   d) if the acceptance criteria are satisfied making a further variation to the varied set of multileaf collimator configurations;
   e) if the acceptance criteria are not satisfied, rejecting a most recent variation to the varied set of multileaf collimator configurations; and,
   f) repeating (b) through (e) until the varied set of multileaf collimator configurations satisfies one or more termination criteria;
      wherein each of the multileaf collimator configurations comprises a different rotational angle for the multileaf collimator relative to a direction of a radiation beam to be delivered through the multi-leaf collimator.

24. A computer readable medium comprising computer-readable instructions which, when executed by a data processor, cause the data processor to execute a method comprising:
   a) varying a parameter of an initial set comprising three or more multileaf collimator configurations to provide a varied set of multileaf collimator configurations;
   b) determining a calculated radiation field resulting from the varied set of multileaf collimator configurations;
   c) based upon the calculated radiation field determining whether one or more acceptance criteria are satisfied;
   d) if the acceptance criteria are satisfied making a further variation to the varied set of multileaf collimator configurations;
   e) if the acceptance criteria are not satisfied, rejecting a most recent variation to the varied set of multileaf collimator configurations; and,
   f) repeating (b) through (e) until the varied set of multileaf collimator configurations satisfies one or more termination criteria;
      wherein each of the multileaf collimator configurations comprises a different rotational angle for the multileaf collimator relative to a direction of a radiation beam to be delivered through the multi-leaf collimator.

25. A method for controlling a radiation device to deliver an intensity modulated radiation field to a treatment area, the intensity modulated field having a spatial distribution of radiation according to a treatment plan, the method comprising:
   delivering in succession at least three radiation sub-fields, each of the sub-fields shaped by a multileaf collimator and each of the sub-fields directed in the same spatial direction; and,
   rotating the collimator to a different angular position about the spatial direction for the delivery of each of the sub-fields;
   wherein one of the different angular positions is non-orthogonal to at least two other ones of the different angular positions; and,
   wherein the sub-fields sum to yield the intensity modulated field that delivers a spatially non-uniform radiation dose within the treatment area according to the treatment plan.

26. A method according to claim 25 where rotating the multileaf collimator is performed in a plane of the multileaf collimator.

27. A method according to claim 25 wherein each of the sub-fields is defined by a different configuration of leaves in the multileaf collimator and the method comprises using an optimization algorithm to derive one or more treatment parameters, the treatment parameters including the different configurations of leaves.

28. A method according to claim 27 wherein using the optimization algorithm comprises modifying an initial set of treatment parameters.

29. A method according to claim 28 wherein modifying an initial set of treatment parameters comprises randomly selecting and modifying parameters of the initial set of treatment parameters.

30. A method for operating a radiation device, the method comprising;
   issuing a first portion of radiation through a multileaf collimator the multileaf collimator disposed in a plane, wherein the first portion of radiation is issued in a direction substantially normal to the plane when the multileaf collimator is oriented at a first angular position about an axis of rotation substantially normal to the plane;
   rotating the multileaf collimator about the axis of rotation; and
   issuing a second portion of radiation through the multileaf collimator when the multileaf collimator is disposed in the plane and a rotated about the axis of rotation through an acute angle relative to the first angular position.

31. A method according to claim 30 comprising rotating the multileaf collimator about the axis of rotation while issuing: the first portion of radiation, the second portion of radiation, or both the first and second portions of radiation.

32. A method according to claim 30 comprising issuing the second portion of radiation during a time interval when the multileaf collimator is rotating about the axis of rotation.

33. A method according to claim 32 comprising delivering a statically provided sub-field by issuing a third portion of radiation with the multileaf collimator stationary and rotated about the axis of rotation through the acute angle relative to the first angular position.

34. A method according to claim 30 wherein the multileaf collimator is stationary while the second portion of radiation is delivered.

35. A method according to claim 34 wherein the multileaf collimator is stationary while the first portion of radiation is delivered.

36. A method according to claim 30 comprising controlling the multileaf collimator to have a first configuration of leaves during delivery of the first portion of radiation and controlling the multileaf collimator to have a second configuration of leaves different from the first configuration of leaves during delivery of the second portion of radiation.

37. A method according to claim 30 comprising, after issuing the second portion of radiation, controlling the radiotherapy device to successively issue a series of one or more additional portions of radiation, the method comprising, for each of the successive additional portions of radiation, controlling the multileaf collimator to rotate about the axis of rotation through an acute angle and subsequently issuing the additional portion of radiation.

38. A method according to claim 37 wherein the acute angles between the successive additional portions of radiation do not exceed 4 degrees.

39. A method according to claim 30 comprising adjusting a rotational position of a rotating gantry to achieve a desired orientation of the direction of the first portion of radiation relative to a subject.

40. A method for controlling a radiation device to deliver a radiation field having a desired spatial distribution of radiation, the method comprising:
controlling a radiation beam of the radiation device to deliver in succession two or more radiation subfields each shaped by a multileaf collimator, the multileaf collimator rotatable relative to a direction of the radiation beam; and,
for the delivery of each of the sub-fields, positioning the multileaf collimator at a different angular position about the direction of the radiation beam while maintaining the direction of the radiation beam constant;
wherein at least two of the different angular positions are oriented an acute angle relative to one another.

41. A method according to claim 40 wherein controlling the radiation beam of the radiation device to deliver in succession two or more radiation subfields comprises controlling the radiation beam of the radiation device to deliver three or more radiation subfields.

42. A method according to claim 40 comprising controlling the multileaf collimator to have a first configuration of leaves during delivery of the first portion of radiation and controlling the multileaf collimator to have a second configuration of leaves different from the first configuration of leaves during delivery of the second portion of radiation.

43. A method according to claim 42 wherein the multileaf collimator is stationary during delivery of a first one of the radiation sub-fields.

44. A method according to claim 43 wherein the multileaf collimator is stationary during delivery of each of the radiation sub-fields.

45. A method according to claim 40 comprising adjusting a rotational position of a rotating gantry to achieve a desired orientation of the direction of the radiation beam relative to a subject.

46. A method for operating a radiation device to produce a desired radiation field, the method comprising:
in a radiation device comprising a multileaf collimator disposed in a plane, successively issuing a plurality of portions of radiation through the multileaf collimator in a direction substantially normal to the plane while rotating the multileaf collimator about an axis of rotation substantially normal to the plane, wherein issuing each of the plurality of portions of radiation is done while the collimator is being rotated through a different angular range.

47. A method according to claim 46 comprising altering a configuration of leaves of the multileaf collimator while rotating the multileaf collimator about the axis of rotation.

48. A method according to claim 46 comprising rotating the multileaf collimator by an angle not exceeding 4 degrees between initiating issuing successive ones of the plurality of portions of radiation.

49. A method according to claim 46 comprising rotating the multileaf collimator by an angle in the range of 0.2 to 2 degrees between initiating issuing successive ones of the plurality of portions of radiation.

50. A method according to claim 46 comprising adjusting a rotational position of a rotating gantry to achieve a desired orientation of the direction of the portions of radiation relative to a subject.

51. A method for operating a radiation device, the method comprising;
issuing a first portion of radiation through a multileaf collimator, the multileaf collimator disposed in a plane, wherein the first portion of radiation is issued in a direction substantially normal to the plane and the multileaf collimator is at a first angular position;
rotating the multileaf collimator about an axis of rotation substantially normal to the plane; and,
issuing a second portion of radiation through the multileaf collimator when the multileaf collimator is at a second angular position;
wherein, a position of an imaginary reference line in the plane, fixed to the multileaf collimator and intersecting with the axis of rotation of the multileaf collimator when the multileaf collimator is in the second angular position forms an acute angle at the axis of rotation with a position of the imaginary line when the multileaf collimator is in the first angular position.

52. A method according to claim 51 comprising rotating the multileaf collimator through an angle in excess of 90 degrees between issuing the first and second portions of radiation.

53. A method according to claim 51 comprising rotating the multileaf collimator about the axis of rotation while issuing: the first portion of radiation, the second portion of radiation, or both the first and second portions of radiation.

54. A method according to claim 53 comprising delivering a statically provided sub-field by issuing a third portion of radiation with the multileaf collimator stationary and in the second angular position.

55. A method according to claim 51 comprising issuing the second portion of radiation during a time interval when the multileaf collimator is rotating.

56. A method according to claim 51 wherein the multileaf collimator is stationary to claim 51 second portion of radiation is delivered.

57. A method according to claim 56 wherein the multileaf collimator is stationary while the first portion of radiation is delivered.

58. A method according to claim 51 comprising controlling the multileaf collimator to have a first configuration of leaves during delivery of the first portion of radiation and controlling the multileaf collimator to have a second configuration of leaves different from the first configuration of leaves during delivery of the second portion of radiation.

59. A method according to claim 51 comprising, after issuing the second portion of radiation, controlling the radiotherapy device to successively issue a series of one or more additional portions of radiation, the method comprising, for each of the successive additional portions of radiation, controlling the multileaf collimator to rotate about the axis of rotation through an acute angle and subsequently issuing the additional portion of radiation.

60. A method according to claim 51 comprising adjusting a rotational position of a rotating gantry to achieve a desired orientation of the direction of the first portion of radiation relative to a subject.

61. A radiation device comprising:
a source of radiation;
a multileaf collimator disposed in a path of radiation from the source of radiation;

a rotation mechanism connected to controllably rotate the multileaf collimator about a direction of the radiation from the source of radiation;

a control system configured to operate the source of radiation to deliver an intensity modulated radiation field to a treatment area by delivering in succession at least two radiation sub-fields, for each of the sub-fields the control system configured to:

control a mechanism to move leaves of the multileaf collimator to a desired configuration to shape the radiation and operate the rotation mechanism to rotate the multileaf collimator to a desire angular position about the direction of the radiation; and operate the source of radiation to deliver the sub-field;

wherein the angular position of the multileaf collimator is different for each of the sub-fields, angular positions for at least two of the sub-fields are at an acute angle relative to one another and, the intensity modulated radiation field comprises a spatial distribution of radiation that varies over the treatment area in a manner specified by a treatment plan.

62. A radiation device according to claim 61 comprising a gantry, the gantry rotatable to vary the direction of the radiation relative to a subject.

63. A radiation device comprising:

a source of radiation;

a multileaf collimator disposed in a path of radiation from the source of radiation;

a rotation mechanism connected to controllably rotate the multileaf collimator about a direction of the radiation;

a control system configured to operate the source of radiation to deliver a radiation field by successively issuing a plurality of portions of radiation through the multileaf collimator while rotating the multileaf collimator about the direction of the radiation, wherein the control system is configured to cause each of the portions of radiation to be issued while the collimator is being rotated through a different annular range.

64. A radiation device according to claim 63 wherein the control system is configured to successively issue the plurality of portions of radiation through the multileaf collimator while the direction of the radiation remains fixed.

65. A radiation device according to claim 63 wherein the control system is configured to alter a configuration of leaves of the multileaf collimator while the multileaf collimator is rotating.

66. A radiation device according to claim 63 wherein the control system is configured to cause the radiation device to deliver one or more additional portions of radiation by, for each of the additional portions of radiation:

setting a rotational angle of the collimator about the direction of the radiation;

setting a configuration of leaves of the multileaf collimator; and, controlling the radiation source to issue the portion of radiation through the multileaf collimator while the multileaf collimator is not rotating.

67. A radiation device according to claim 63 comprising a gantry, the gantry rotatable to vary the direction of the radiation relative to a subject.

* * * * *